(12) United States Patent
Boyum

(10) Patent No.: US 7,201,579 B1
(45) Date of Patent: Apr. 10, 2007

(54) NUTRITION AND EXERCISE PROGRAM

(76) Inventor: Yasemin Boyum, 5710 1/2 Sherier Pl., Washington, DC (US) 20016

( * ) Notice: Subject to any disclaimer, the term of this patent is extended or adjusted under 35 U.S.C. 154(b) by 260 days.

(21) Appl. No.: 10/418,070

(22) Filed: Apr. 18, 2003

Related U.S. Application Data

(60) Provisional application No. 60/373,306, filed on Apr. 18, 2002.

(51) Int. Cl.
*G09B 19/00* (2006.01)

(52) U.S. Cl. .................................................. 434/127

(58) Field of Classification Search ............... 434/127, 434/262; 600/300; 206/561, 562, 564; 426/87, 426/119, 120
See application file for complete search history.

(56) References Cited

U.S. PATENT DOCUMENTS

| | | | |
|---|---|---|---|
| D16,633 S | 4/1886 | Gerard | |
| 3,708,086 A | 1/1973 | Colato | |
| 3,841,260 A * | 10/1974 | Sharp et al. | 116/325 |
| 4,075,769 A | 2/1978 | Young | |
| D281,849 S * | 12/1985 | Cantor | D7/555 |
| 4,625,675 A * | 12/1986 | Rosenberg | 116/324 |
| 4,689,019 A * | 8/1987 | Tilney | 434/127 |
| 4,950,164 A * | 8/1990 | Lennon-Thompson et al. | 434/127 |
| 5,236,119 A | 8/1993 | Chu | |
| 5,328,051 A | 7/1994 | Potter et al. | |
| 5,338,202 A * | 8/1994 | Saari | 434/127 |
| 5,382,165 A * | 1/1995 | Knox | 434/127 |
| 5,402,679 A | 4/1995 | Vogel | |
| 5,454,721 A | 10/1995 | Kuch | |
| 5,560,653 A * | 10/1996 | Beppu | 283/117 |
| 5,593,062 A | 1/1997 | Martin | |
| 5,683,251 A * | 11/1997 | Logan et al. | 434/127 |
| 5,925,390 A * | 7/1999 | Kornacki | 426/87 |
| 6,065,393 A * | 5/2000 | Lombard et al. | 99/427 |
| 6,296,488 B1 * | 10/2001 | Brenkus et al. | 434/127 |
| 6,431,873 B1 * | 8/2002 | Flagg | 434/127 |
| 6,553,386 B1 * | 4/2003 | Alabaster | 707/104.1 |

FOREIGN PATENT DOCUMENTS

GB 2119633 * 11/1983

* cited by examiner

*Primary Examiner*—Kurt Fernstrom
(74) *Attorney, Agent, or Firm*—Hoffman, Wasson & Gitler

(57) ABSTRACT

An exercise nutritional program focuses on overall health of the user and is part of an overall fitness regimen including exercise. Proper weight and weight maintenance is an ancillary benefit of following a nutritional program and will be achieved by years of following the nutrition program in conjunction with the exercise and fitness program. The nutritional program separates foods into carbohydrates, proteins and fats and adjusts the percent of calories from each group depending on the goal of general weight maintenance, increased shape and definition or significant weight loss. An exercise program is also tailored to these three goals. In implementing the program, three connected shapes, preferably rings, or containers, representing the carbohydrate, protein and fat groups are used. Each ring is desirably a different color so that the user can readily ascertain which ring corresponds to which food group listed on the menus provided. The frequency of using these rings depends on the individual's goals in fitness.

6 Claims, 4 Drawing Sheets

NUTRITION AND EXERCISE PROGRAM

This application claims the benefit of provisional application 60/373,306, filed Apr. 18, 2002.

FIELD OF THE INVENTION

A nutritional program and apparatus for implementing the program.

BACKGROUND OF THE INVENTION

Many exercise nutritional plans have been developed and published. The majority of the programs deal with weight loss and weight maintenance. This fact is a result of obesity being a major problem in the United States. These programs focus on the daily caloric intake of the person following the program to reduce and maintain a desirable weight and avoid the numerous health problems related with obesity.

Nutritional and exercise programs need to be easy to understand and follow and provide results if it can be reasonably expected for user's to follow the program for extended periods of time and not deviate from the program. A complete nutritional program needs to encompass both the type of food being eaten and the portions of the food. The program must also include an easy to follow guide so that the user is assured of fitting within the boundaries and parameters set forth by the nutritional program.

It is an object of the invention to provide a nutritional program that is part of an overall fitness regimen.

It is another object of the invention to provide a nutritional program having a device enabling the implementation of the program.

It is yet another object of the invention to provide a portion control device for the various types of foods fitting within the program.

It is still another object of the invention to provide a nutrition program which is complete, easy to follow and provide results to the user.

These and other objects will become apparent to one of ordinary skill in the art after reviewing the disclosure of the invention.

SUMMARY OF THE INVENTION

An exercise nutritional program focuses on overall health of the user and is part of an overall fitness regimen including exercise. Proper weight and weight maintenance is an ancillary benefit of following a nutritional program and will be achieved by years of following the nutrition program in conjunction with the exercise and fitness program. The nutritional program separates foods into carbohydrates, proteins and fats and adjusts the percent of calories from each group depending on the goal of general weight maintenance, increased shape and definition or significant weight loss. An exercise program is also tailored to these three goals. In implementing the program, three connected shapes, preferably rings, or containers, representing the carbohydrate, protein and fat groups are used. Each ring is desirably a different color so that the user can readily ascertain which ring corresponds to which food group listed on the menus provided. The frequency of using these rings depends on the individual's goals in fitness.

DETAILED DESCRIPTION OF THE INVENTION

Figure 1:
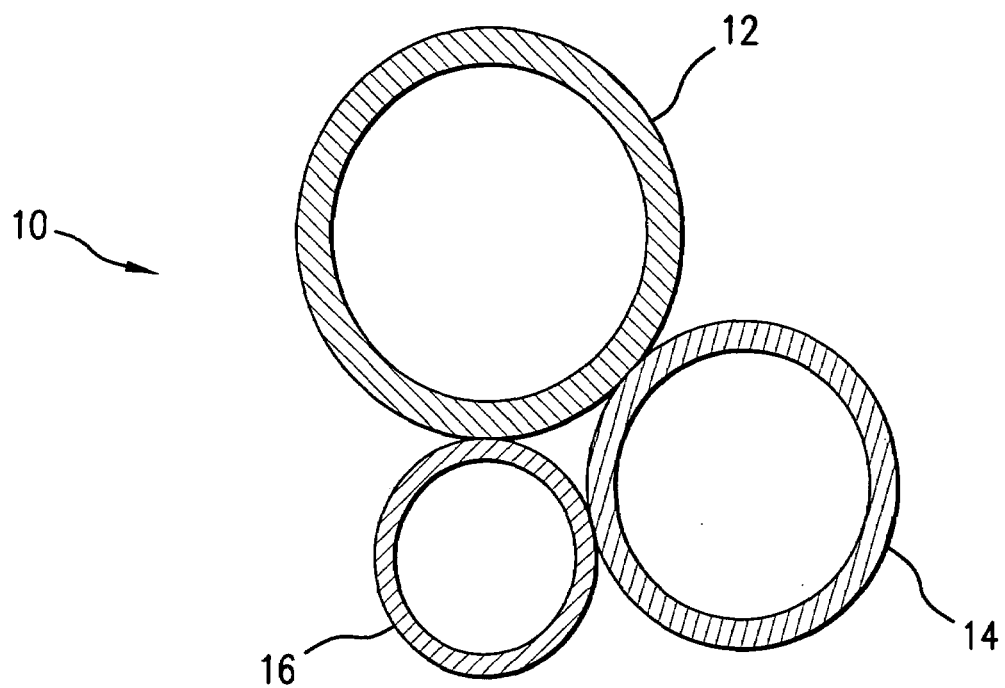
FIG. 1 depicts the connected rings used in implementation of the nutritional program.

The nutrition and fitness regimen includes a nutritional program, aerobic workout and weight resistance training. Proper nutrition includes eating four to five small meals throughout the course of the day, without overeating at any one meal. Carbohydrate intake is kept to an absolute minimum at night due to the body's slower metabolic rate. The use of several small meals increases the body metabolism, helping the body to burn more calories.

The aerobics workout burns fat, strengthens the cardiovascular system and helps in the prevention of myocardial infarction (heart attack) and other debilitating illnesses like arteriosclerotic heart disease (ASHD). These to conditions are the leading causes of death in the United States. The best time for aerobic training is the first thing in the morning on an empty stomach so that the body's primary fuel source at that time is fat. Aerobic activity necessitates a steady state of intensity for at least 30 minutes for at least three to four times per week. The intensity would include 65–75% of your maximum target heart rate, usually calculated as 220 minus your age.

Weight training is included to take advantage of its ability to increase bone density, muscle mass, thereby creating highly metabolic active tissue, and the improvement in self-esteem and posture. Weight training can be done any time during the day but is best accomplished one hour after a meal high in carbohydrates.

The nutrition aspect is separated between carbohydrates, proteins and fats. Acceptable foods for the carbohydrate portions include sweet potatoes, oatmeal, brown rice and cream of rice. Appropriate foods for the protein category include chicken, tuna, meat, lentils, fish, egg whites and turkey breast. The list of appropriate fat foods includes peanut butter (one tablespoon), rice pudding (½ cup), nuts/pistachios or almonds (15–20 nuts) and avocado dip (two tablespoons). Foods which do not fit under the plan in any category include bread, pasta, bagels, cereals, chips, cookies, sugar products or any flour product. There are alternative options to those who may be diabetic or hypoglycemic.

Three levels of the regimen have been established. The three levels are summarized on the chart below and include a first row for general weight maintenance, a second row for increased shape and definition, and a third row for significant weight loss.

| FITNESS CHART | | |
|---|---|---|
| NUTRITION (% of Calories) | AEROBICS (Frequency/Time) | WEIGHT TRAINING (Frequency/Type) |
| 50% carbohydrates 25% protein 25% fats | 3 times/week 30 min. | 3 days/week total body |

-continued

FITNESS CHART

| NUTRITION (% of Calories) | AEROBICS (Frequency/Time) | WEIGHT TRAINING (Frequency/Type) |
|---|---|---|
| 45% carbohydrates | 4 times/week | 4 days/week |
| 30% protein | 40 min. | split routine |
| 25% fats | | upper body/lower body |
| 35–40% carbohydrates | 5–6 times/week | 4–5 days/week |
| 35–40% protein | 45 min. to 1 hr. | split routine |
| 15–20% fats | | all muscle groups worked separately on certain days |

Figure 2:
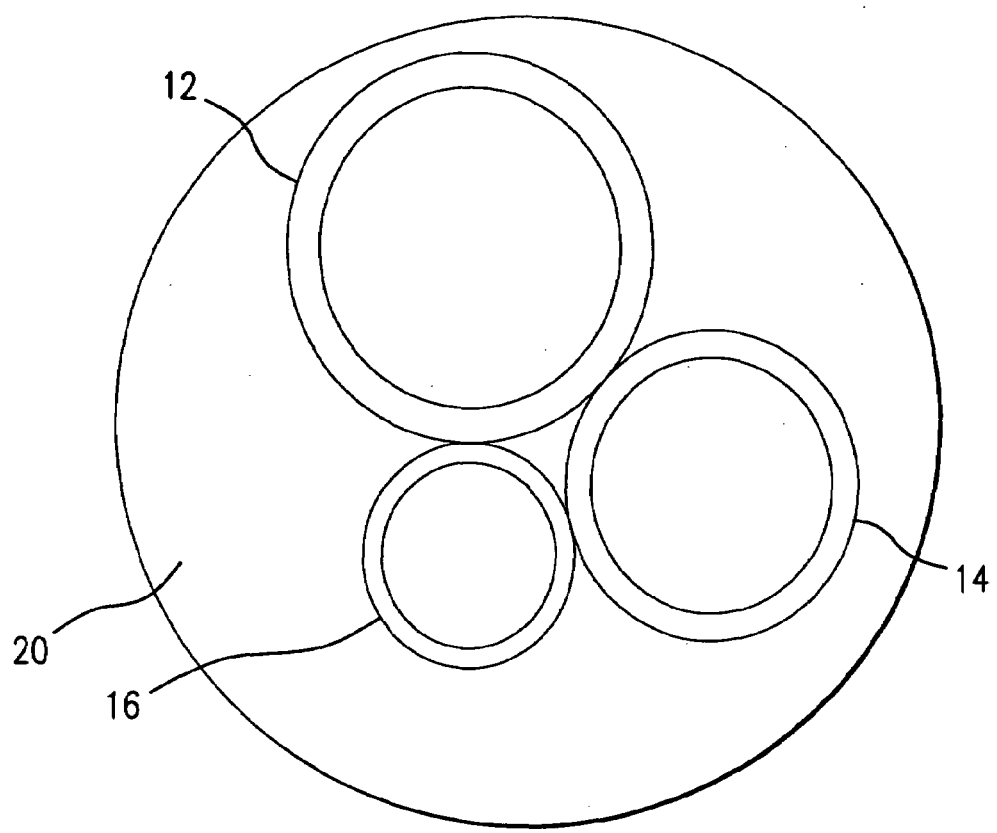
FIG. 2 shows three connected or bound rings formed as an integral part of a plate.

To implement the nutritional aspect of the program, three connected rings 10 are used. The three connected rings are shown in FIG. 1. The carbohydrate ring 12 is 3.5 inches in diameter, the protein ring 14 is 3 inches and the fat ring 16 is 2 inches. Each ring is color coded to signify to the user which ring corresponds to which food group. In the embodiment shown in FIG. 1, the three rings can be placed on any plate. This allows the rings to be used with any variety of plates. Alternatively, the rings can be formed integrally with a plate 20 as shown in FIG. 2. This one piece construction allows the use of the rings without having to use a separate plate.

Figure 3:
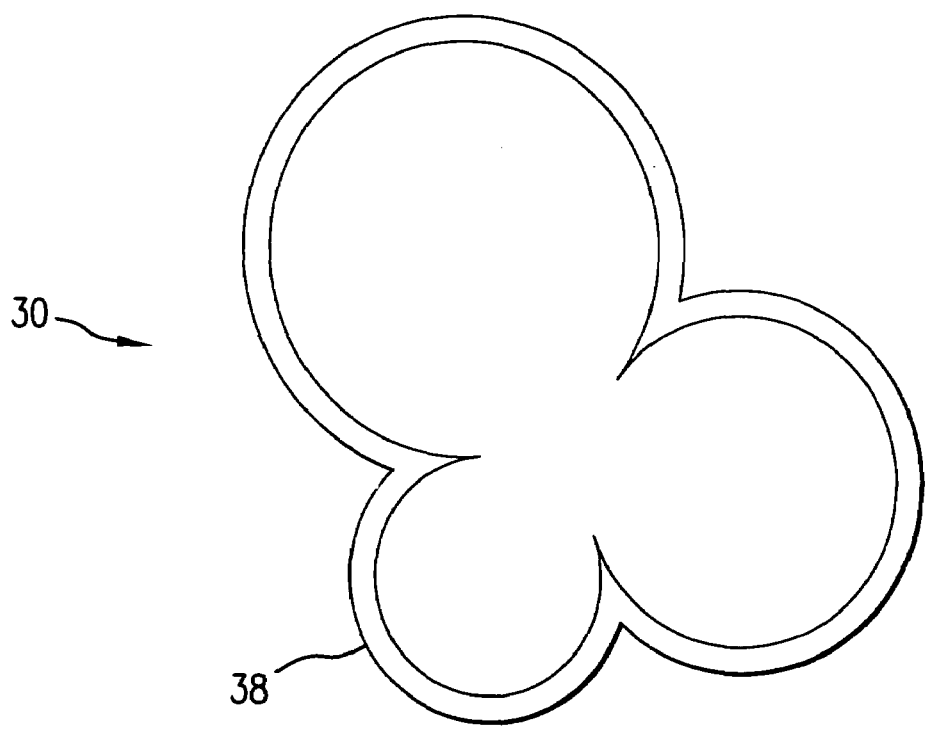
FIG. 3 depicts a cover for the rings.

A cover 30 for the rings is shown in FIG. 3. The cover has a shape corresponding to the outer periphery of the three connected rings. A flange 38 depends from the top wall and engages the sides of the rings to releasably retain the cover on the rings. The cover can take the form of a top panel as large as the plate with a depending flange engaging the outer periphery of the rings.

Figure 4:
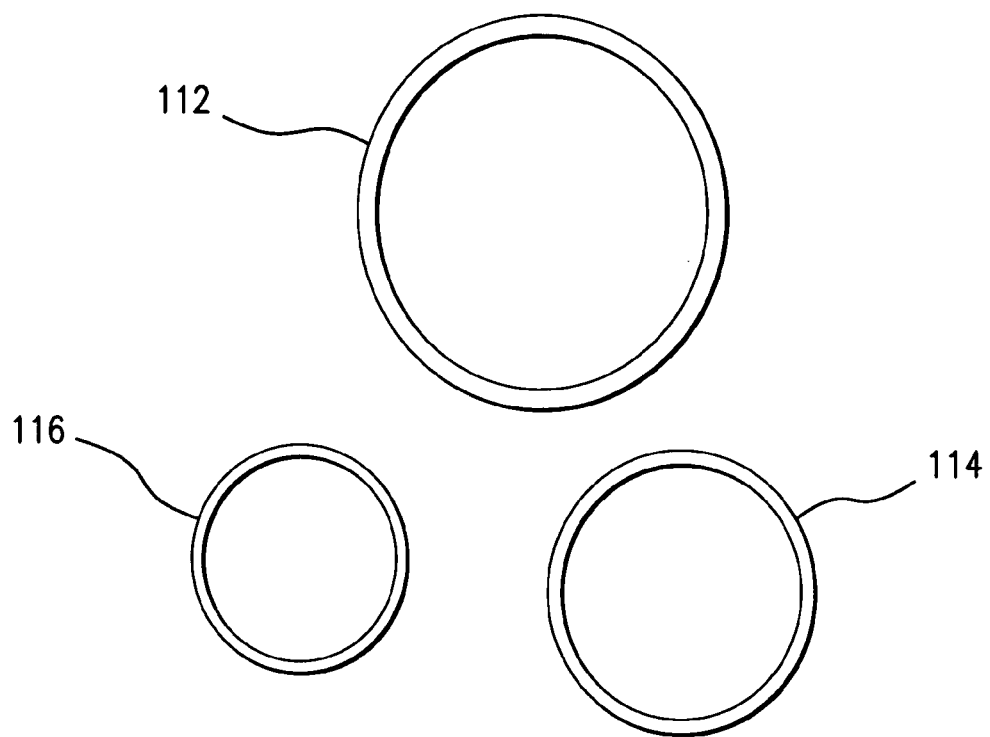
FIG. 4 depicts the embodiment of the invention having three separated rings.

A second embodiment of the invention is depicted in FIG. 4. In this invention, the three rings are separate. The largest ring 112 is for foods of the carbohydrate group, the medium ring 114 is for foods in the protein group and the smallest ring 116 is for foods of the fat group. This allows the rings to be used with any conventional dinner plate. The size of the rings and the color of the rings is identical to that of the first embodiment having connecting rings. The size of the rings is again proportioned to the amount of that food group you should consume and the color of the rings is color coded to the accompanying menu.

While the invention has been discussed with reference to preferred embodiments, variations and modifications would be apparent to one of ordinary skill in the art which would not deviate from the scope and spirit of the invention, the invention encompasses such variations and modifications.

What is claimed is:

1. A nutritional program, comprising:
    a first ring having a first color;
    a second ring having a second color;
    a third ring having a third color,
    said first, second and third rings tangentially connected to one another, each being a different size and having no bottom wall.

2. The nutritional program of claim 1, wherein said first ring is the smallest ring and said third ring is the largest ring.

3. The nutritional program of claim 1, further comprising a cover for said rings.

4. The nutritional program of claim 1, further comprising a menu listing foods belonging to fat groups, protein group and carbohydrates group.

5. The nutritional program of claim 4, further comprising a menu listing foods belonging to said fat group, said protein group and said carbohydrate group, said listing of foods color coded to correlate the food with the color of said rings.

6. A nutritional program, comprising:
    a first ring;
    a second ring;
    a third ring,
    said first, second and third rings tangentially connected to one another, each being a different size and having no bottom wall.

* * * * *